Dec. 31, 1946. F. H. HOWARD Plant Pat. 721
PLUM TREE
Filed March 5, 1946
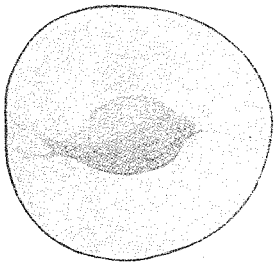
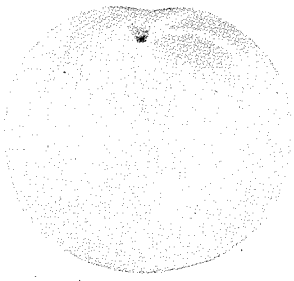
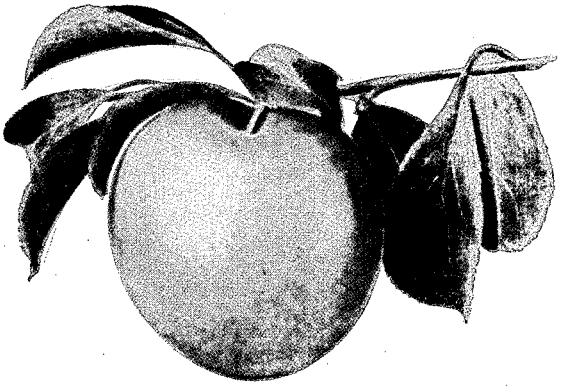
INVENTOR
Frederick Huber Howard
By Orville M. Kile
Plant Pat. Agt.

Patented Dec. 31, 1946

Plant Pat. 721

UNITED STATES PATENT OFFICE

721

PLUM TREE

Frederick Huber Howard, Montebello, Calif., assignor to Howard & Smith, Montebello, Calif.

Application March 5, 1946, Serial 652,015

1 Claim. (Cl. 47—62)

My present discovery relates to a new and useful variety of plum tree, with particular reference to the fruit produced by the tree.

My new variety of plum tree originated as a volunteer chance seedling which occurred in a garden wherein only two plum trees were set—one an old-fashioned Green Gage, and the other a Satsuma. These two trees were set close together and apparently the present variety is a hybrid resulting from a natural cross of these two varieties. The new variety has some of the characteristics of each of these varieties but is entirely distinct and different from them or any other variety of plum known to me.

The fruit of my new variety is large, the pit small, the flavor definitely distinctive, the color brilliant, and the keeping and shipping qualities excellent.

Asexual reproduction of the variety for some years has proved the distinctive qualities of the variety to be firmly fixed.

The accompanying illustration shows, from top to bottom, a cross section of the fruit, a fully ripened fruit, and a partially ripened fruit attached to a small branch of foliage.

Following is a detailed description of the tree and fruit of this new variety, in which color plate numbers refer to Ridgway's Color Standards and Nomenclature. Where no color plate number is given, the ordinary dictionary meaning of the term is intended.

*The tree*

Growth: Extremely ramulose. Tremendous grower. Much more vigorous than most other plum varieties grown in southern California.
Form: Upright; somewhat spreading.
Branches: Smooth.
Twigs: Long and slender. Of slightly reddish hue.
Nodes: Very prominent and evenly spaced.
Production of fruit: Average, compared with such varieties as Burbank, Santa Rosa, Satsuma, etc.
Foliage:
- *Shape of leaves.*—Oblong-obovate, acute, pointed at apex. Margins crenulate-serrulate. Leaves inclined to fold at midrib.
- *Color.*—Dark green and lustrous above; slightly lighter on under side.
- *Texture and veining.*—Heavy.
- *Petioles.*—Short.

Blossoms: Similar to those of the Satsuma variety.

*Fruits*

Maturity season: Late; usual ripening dates in southern California are approximately July 15th to August 1st.

Borne: More or less in clusters.
Form: Round-cordate; halves equal; cavity shallow.
Size: Large, measuring about 2¼ inches in diameter.
Skin:
- *Adherence.*—Moderate. Skin can easily be peeled off when fruit is ripe.
- *Texture.*—Smooth; tough; thin.
- *Color.*—Approaching maturity, the color is light red with a slight suffusion of yellow on portions of the skin. Just prior to this the skin is approximately Eugenia Red (Pl. XIII). When fruit reaches maturity it is a golden color overlaid with a slight suffusion of red. This plum is sometimes spoken of as the plum with the maple leaved color.

Flesh:
- *Color.*—Amber yellow, almost white. Translucent.
- *Firmness.*—Very firm; stands shipping well and is an excellent keeper.
- *Texture.*—Free of any stringiness.
- *Juice.*—Exceedingly juicy. More juicy than any other plum known to me, being in that respect equal to a well ripened Hale peach.
- *Flavor.*—Unlike that of any known plum. The flavor is difficult to describe but many describe it as nectar-like. Some persons have likened it to pineapple flavor, others to a combination of ordinary plum with nectarine.

Stone:
- *Size.*—Small, measuring approximately ¾ inch long and ⅜ to ½ inch wide.
- *Shape.*—Oblong; regular.
- *Surface.*—Smooth or only slightly corrugated.
- *Color.*—Light brown.
- *Adherence.*—Freestone. Pits are easily removable without adhering flesh.
- *Stem.*—Very short.

Having thus disclosed my discovery, I claim:

The new and distinct variety of plum tree substantially as shown and described, characterized particularly by its fast and vigorous growth; its late ripening season; its large fruits with small pits, clear firm pale yellow flesh of distinctive flavor and great juiciness, and skin displaying varying amounts of yellow and light red according to maturity stages; as well as the excellent keeping qualities of its fruits.

FREDERICK HUBER HOWARD.